US008411921B2

(12) United States Patent
Boese et al.

(10) Patent No.: US 8,411,921 B2
(45) Date of Patent: Apr. 2, 2013

(54) DEVICE AND METHOD FOR SYNCHRONIZING AN IMAGE CAPTURE DEVICE WITH A PRE-OPERATIVE IMAGE DATA SET

(75) Inventors: Jan Boese, Eckental (DE); Andreas Meyer, Möhrendorf (DE); Norbert Rahn, Forchheim (DE); Bernhard Sandkamp, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1324 days.

(21) Appl. No.: 11/725,517

(22) Filed: Mar. 19, 2007

(65) Prior Publication Data
US 2007/0248262 A1 Oct. 25, 2007

(30) Foreign Application Priority Data

Mar. 23, 2006 (DE) .................. 10 2006 013 475

(51) Int. Cl.
*G06K 9/00* (2006.01)
(52) U.S. Cl. ............ 382/131; 382/128; 382/132; 378/4; 600/407; 600/428; 600/509; 600/513
(58) Field of Classification Search .................. 382/128, 382/131, 132; 378/4; 600/407, 428, 509, 600/513
See application file for complete search history.

(56) References Cited

U.S. PATENT DOCUMENTS

| 6,298,260 | B1 * | 10/2001 | Sontag et al. ........... 600/413 |
| 6,381,487 | B1 * | 4/2002 | Flohr et al. ............ 600/425 |
| 6,721,386 | B2 * | 4/2004 | Bulkes et al. ............ 378/8 |
| 6,865,248 | B1 | 3/2005 | Rasche et al. |
| 7,474,913 | B2 * | 1/2009 | Durlak ................ 600/428 |
| 7,684,848 | B2 * | 3/2010 | Kuhara et al. ........... 600/413 |
| 2003/0007593 | A1 * | 1/2003 | Heuscher et al. .......... 378/4 |
| 2003/0032887 | A1 * | 2/2003 | Harada et al. ........... 600/513 |
| 2003/0128801 | A1 * | 7/2003 | Eisenberg et al. ........ 378/19 |
| 2003/0199748 | A1 * | 10/2003 | Camus et al. ........... 600/407 |
| 2004/0077941 | A1 * | 4/2004 | Reddy et al. ........... 600/428 |
| 2004/0097805 | A1 * | 5/2004 | Verard et al. ........... 600/428 |
| 2005/0137661 | A1 * | 6/2005 | Sra ................... 607/96 |
| 2005/0148836 | A1 | 7/2005 | Kleen et al. |
| 2005/0251028 | A1 | 11/2005 | Boese et al. |

FOREIGN PATENT DOCUMENTS

| CA | 2 445 360 A1 | 10/2003 |
| DE | 199 46 092 A1 | 3/2001 |
| DE | 103 55 275 A1 | 7/2005 |
| DE | 10 2004 020 587 A1 | 11/2005 |
| EP | 1 310 913 A1 | 5/2003 |
| EP | 1 350 470 B1 | 10/2003 |

* cited by examiner

*Primary Examiner* — Matthew Bella
*Assistant Examiner* — Julian Brooks

(57) ABSTRACT

The present invention relates to a device and a method for synchronizing an image capture device with a first image data set. The image capture device is used for recording a second image data set of a periodically moving area or object. Each first image data set contains information as to the point in time, relative to the periodically moving area or object, when recording took place. The device additionally acquires periodically recurring, current information of the area as well as information concerning the recording instant of the first image data set. From the periodically recurring information and the recording instant of the first image data set, a triggering instant is derived which controls at least one recording of the second image data set by the image capture device in such a way that the second image data set contains image data synchronized to the first image data set.

20 Claims, 2 Drawing Sheets

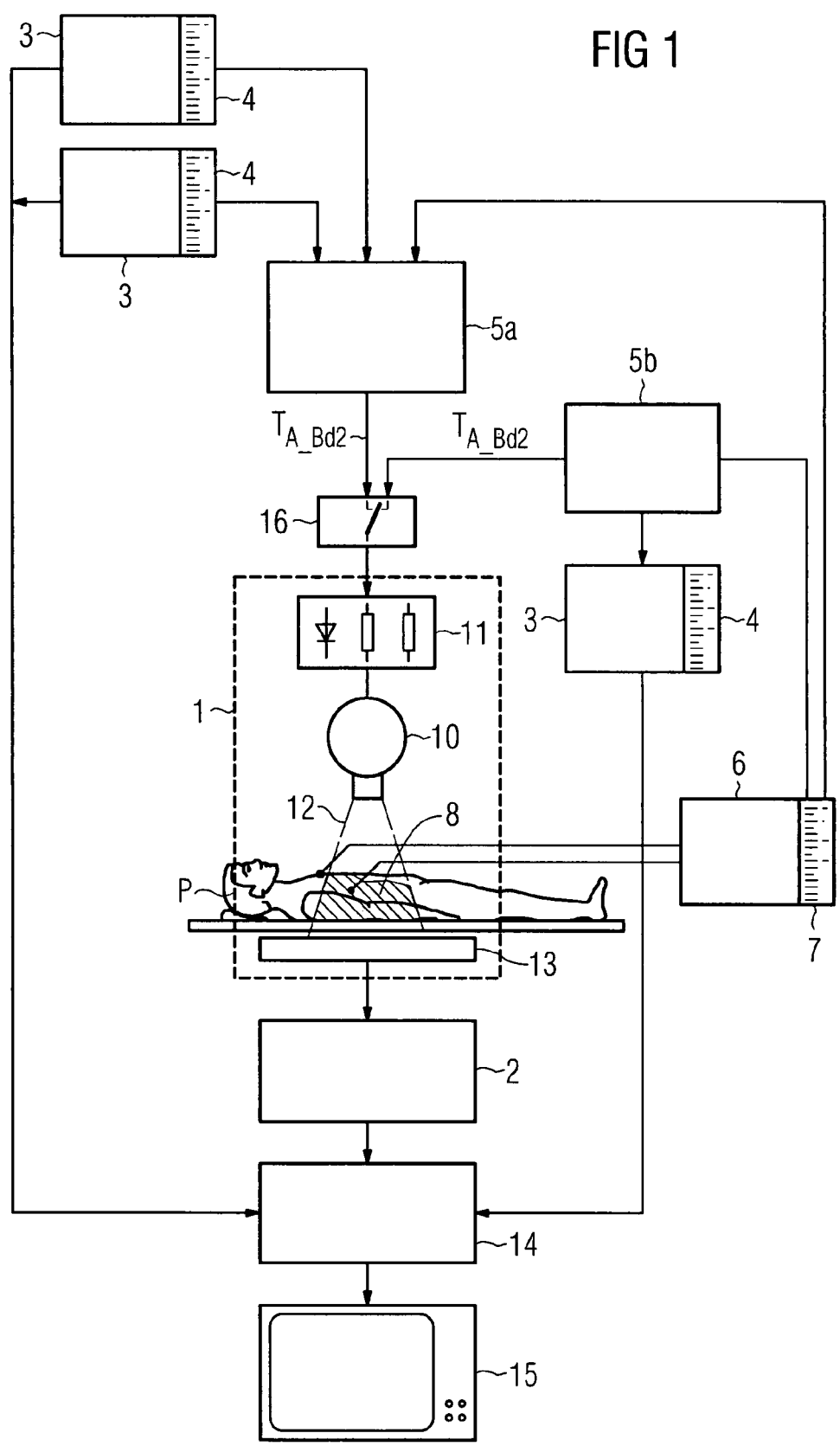

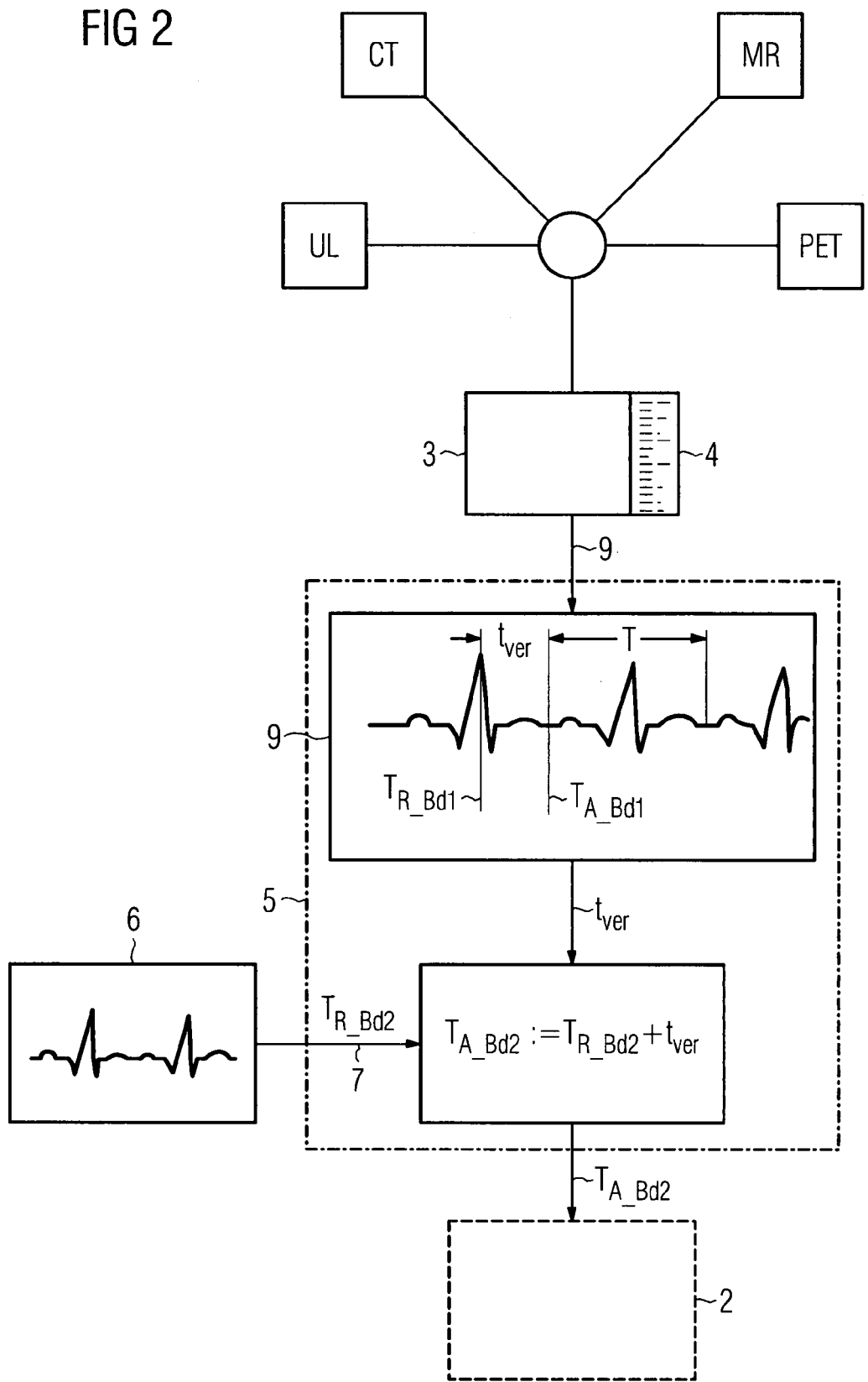

DEVICE AND METHOD FOR SYNCHRONIZING AN IMAGE CAPTURE DEVICE WITH A PRE-OPERATIVE IMAGE DATA SET

CROSS REFERENCE TO RELATED APPLICATIONS

This application claims priority of German application No. 10 2006 013 475.3 filed Mar. 23, 2006, which is incorporated by reference herein in its entirety.

FIELD OF THE INVENTION

The present invention relates to a device and method for synchronizing an image capture device with a first image data set. The image capture device is used for recording a second image data set of a periodically moving area or periodically moving object. Each first image data set contains information as to the point in time, relative to the periodically moving area or object, when recording took place. The device also has means of acquiring periodically recurring, current information of the area as well as information concerning the recording instant of the first image data set.

BACKGROUND OF THE INVENTION

In medical engineering, for example, image-assisted interventional methods have long played an important role. This applies particularly to surgical interventions on a patient where surgical instruments such as laparoscopes, endoscopes, needle robots, etc. are controlled via various image-assisted methods.

Thus in the simplest case, purely image-assisted positioning of medical instruments is performed, i.e. instrument positioning takes place by direct visual display, i.e. is carried out and monitored on the basis of the images. Examples of this are needle guidance e.g. for biopsies or HF ablations by means of ultrasound, CT-fluoroscopy or x-ray fluoroscopy. These methods are characterized by real-time capability and are currently standard in many fields of application.

Another widely practiced method in medical engineering is the use of surgical navigation based on pre-operative images. In this case instrument positioning is performed with the aid of navigation systems using patient image data acquired prior to the actual operation. This image data is generally based on CT or MR images, but SPECT (Single Photon Emission Computed Tomography) or PET (Positron Emission Tomography) images are also being increasingly used. Operating methods based on pre-operative images are used in orthopedic robotics. Examples of robot-assisted surgical interventions are knee and hip operations. In the prior art, such interventions are performed exclusively using CT x-ray images taken of the area to be operated on prior to the surgical intervention.

However, other interventions in which changes of position occur or may occur may require continuous control images during the intervention in order to ensure safe positioning e.g. of the medical instruments and therefore safe performance of the operation. In this case image data sets are additionally combined with one another during the intervention by if necessary recording new images of the patient during the operation and inserting both into existing 3D image data sets. The use of such a medical method for assisting surgical interventions on a patient is also particularly called for when the surgeon's view of the patient end of a medical instrument guided by him which is inserted in the patient's body is obstructed and/or a position and shape of a body part or organ shown in the previously recorded image does not coincide with the actual position and shape of the body part or organ during the operation.

The abovementioned problem of change of position becomes even more acute when not only one-off position shifts after pre-operative image recordings are involved, but when moving organs must be recorded using imaging methods. This basically relates to the heart with its blood-supplying coronary arteries, heart beat and respiration generally being responsible for such movements.

Every contraction of the cardiac muscle and therefore every pumping function of the heart is preceded by an electrical stimulus. This electrical potential variation across the heart can be picked up on the surface of the body. The movement of the heart caused by contraction of the cardiac muscle therefore occurs periodically and essentially in synchronism with the so-called surface ECG (electrocardiogram). Therefore, sections of the ECG can be assigned to particular periodically recurring, identical phases of cardiac movement. This fact is already used in many examination techniques using imaging methods and is therefore prior art. Examples include cardiac CT or electroanatomical mapping with the Carto system. Systems of this kind enable the user to control image acquisition or the recording of electroanatomical maps of the patient's heart using and as a function of the ECG. The EGG produces a trigger signal normally at the instant of the R-spike. However, this trigger signal therefore unfortunately occurs in the strongest phase of cardiac movement and is therefore unsuitable for image acquisition as, in order to minimize motion artifacts, image data should be recorded in as quiet a movement phase of the heart as possible. In simple form, the acquisition of image data is therefore shifted manually with respect to a characteristic point of the ECG by means of an adjuster. This produces image data (generally 3D image data) recorded in a particular phase of cardiac movement.

As mentioned in the introduction, interventional procedures frequently involve overlaying this pre-operatively recorded 3D image data with 2D image data, thereby enabling the physician performing the intervention to be supplied with additional information from the 3D image data set during the intervention. In another application the physician is given current control images from the 2D image data set, or the position and attitude of medical instruments are to be monitored. For this purpose the 3D image data set must be synchronized with the 2D image data set. Ideally a 2D image data set should therefore be overlaid with the a pre-operatively recorded 3D image data set of the same phase of cardiac movement. For this purpose information is first required as to the cardiac phase in which the 3D image data was generated. The examiner should therefore ideally also be offered a shift of the trigger pulse for the acquisition of the 2D image data. This information is normally specified as a percentage of a period, i.e. 100% being a complete cardiac cycle from R-spike to R-spike. In another form the interval with respect to the R-spike is specified in milliseconds.

In so far as the information about this is available to the examiner, he must control the acquisition of the 2D image data in the same way as for acquisition of the pre-operative 3D image data. As this method must first be disadvantageously preceded by viewing and evaluating the pre-operative image data, this is a very time-consuming and generally also error-prone process. Errors may, however, result in the current image recordings either being poorly synchronized with respect to the pre-operative images and therefore of limited use or in them having to be repeated in their entirety, which in turn results in increased patient dose load.

US 2005/0137661A1 discloses a method and a system using said method for treating cardiac arrhythmias by means of catheter ablation, wherein the CT scanner images of the heart triggered by a patient ECG are reconstructed to produce 3D image data and made available to a central unit of an x-ray machine. The current "live" ECG is likewise recorded and synchronizes the 3D images with the patient's cardiac cycle by detecting the ECG time stamp on the 3D images and comparing the ECG with the corresponding values of the current "live" ECG. In this way the 3D images are therefore synchronized with continuously recorded x-ray images. In a subsequent step a 4D image data set in whose formation only the 2D image data in synchronism with the 3D image data set is involved is then reconstructed and displayed to the interventional team. Although only selected, namely synchronous image data from the same phase of cardiac movement as the pre-operative 3D image data set is involved for reconstructing the 4D image data set produced here, the patient is disadvantageously exposed to a higher radiation dose than is absolutely necessary. In addition, the image capture device itself is caused to make a series of recordings that do not necessarily need to be made.

SUMMARY OF THE INVENTION

The object of the invention is therefore to specify a device and a method for automatically and cost-effectively synchronizing two image data sets which minimizes the recordings by the image capture device and likewise reduces the operating costs of the image capture device. The object of the invention is also to reduce the radiation dose where organisms are directly or indirectly exposed to same.

This object is achieved by a device for synchronizing an image capture device, wherein the image capture device is used for recording a second image data set of a periodically changing area, the second image data set to be synchronized with at least one older first image data set of the area, each first image data set being assignable information as to the point in time, relative to the periodically moving area, when recording takes or took place, said device having means of acquiring periodically recurring current information of the area as well as information concerning the recording instant of the first image data set and being characterized in that, from the periodically recurring current information and the information concerning the recording instant of the first image data set, at least one triggering instant is derived which controls at least one recording of the second image data set by the image capture device in such a way that the second image data set contains image data synchronized to the first image data set.

With reference to the medical engineering field, the abovementioned means can include e.g. a separate central unit which receives, via one interface, information concerning the recording instant of the first image data set. This information is here preferably ECG information used for deriving the triggering instant for activating the image capture device. The information can be combined differently depending on the different image data formats and therefore also the different filing formats of this information. In the abovementioned field of application, the necessary current ECG information of a patient is then read in via another interface. In the simplest case this can be solely the trigger signal of the R-spike. The triggering instant derived or calculated in the central unit is fed out of the central unit and applied to the image capture device, e.g. the x-ray generator of an x-ray machine. The image capture device is therefore controlled automatically and without manual intervention by the interventional team in such a way that current recordings of the patient are only permitted and carried out—i.e. a second image data set is produced—at an instant when the recordings are in synchronism with the first generally pre-operative image data set in respect of the movement phase. The invention is not limited to deriving a triggering instant from the ECG information. Reference is also explicitly made to the possibility of triggering by other physiological parameters in medical engineering such as respiration. In addition, application of the invention to areas outside the medical field e.g. for imaging of oscillating systems would also be conceivable. Unlike in the prior art, the intention here is not to synchronize 3D image data to a continuously generated image data stream, but conversely the recording of the current image data set is synchronized to an older image data set. This also means that the radiation dose to which e.g. the patient must be exposed during the intervention can be reduced to the bare minimum. As the device, in addition, performs the deriving of the triggering signal for the image capture device automatically and without interaction by the examining clinician, the time-consuming and in some cases error-prone evaluation of the first image data set is eliminated and a high degree of synchronization quality is achieved. Interfering motion artifacts are nevertheless minimized.

In an advantageous variant, the device for synchronizing an image capture device is characterized in that a single triggering instant within a period resulting from the periodic movement of the area is derived and controls the image capture device. If the periodically moving area is an area that is stimulated by the heart beat, the image capture device operated in this variant is only activated once per cardiac period. This produces, for example, a frame rate of approximately one frame per second, which is adequate for a large number of applications, the applied x-radiation again being advantageously reduced.

In another variant, the device for synchronizing an image capture device is characterized in that the first image data set was recorded at different recording instants within a period resulting from the periodic movement of the area and the device derives triggering instants $T_{A\_Bd2i}$ which control the image capture device at any of these recording instants. This variant is based on the fact that the generally pre-operative first image data sets have been recorded with a frame rate greater than one frame per period and therefore contain a plurality of frames of a period. As already mentioned elsewhere, a complete period is often set as 100% and the recording or acquisition instant is specified as a percentage (from 0-100%) of said period. In this variant, various recording or acquisition instants are therefore available for the period. For certain applications it may be advisable to control the image capture device, if not at all the acquisition instants of the first image data set, yet in such a way that the image capturedevice is also activated and synchronized image data is therefore present at certain of said acquisition instants. If, for example, the first image data set is recorded at a frame rate of 10 frames per period, the image capture device can, for example, be activated in such a way that, by means of five acquisition instants, either precisely every second image of the first image data set is recorded, or any five images in synchronism with the image data set shall be acquired.

In an advantageous further development of the invention, the device for synchronizing an image capture device is characterized in that the number of first, generally pre-operative image data sets can be recorded using different image recording methods. The critical factor is that the information as to the point in time, relative to the periodic movement of the patient, when the first image data set is recorded is stored in the image data set itself. For medical images such as CT, MR, ultrasound or PET images, this data is stored, for example, together with a number of other data in the header of the image data set saved in DICOM (Digital Imaging and Communication in Medicine) format. However, other image data sets not saved in DICOM format such as electroanatomical maps produced by a Carto system are processed by the inventive device automatically and without interaction by the examining clinician. According to the invention, the device shall be configured in such a way that it is either informed of the type and therefore the format of the data source via an input parameter, or identifies the type and format independently by scanning the data source.

In a further advantageous embodiment of the invention, the device for synchronizing an image capture device is characterized in that the means provided switch between a number of first image data sets. It may be advantageous to insert 2D image data recorded during the intervention into pre-operative image data sets and therefore synchronize them with the latter which have been created using different recording methods. As each recording method has its advantages, but on the other hand also suffers from certain limitations, this enables the interventional team to be provided with optimum image support. The switching and synchronization to various 3D image data sets can take place automatically and sequentially, but quasi-parallel processing would also be possible here. In another variant, switching to another 3D image data set can also take place on demand by the interventional team. In all the abovementioned cases, different display units for the integrated display of the pre-operative and the current image data set are possible, but the use of a single display unit and the control of same using the various integrated image data sets would also be conceivable.

In another embodiment of the invention, the image capture device is characterized in that the means are implemented in an electroanatomical mapping system itself and at least one recording of the second image data set by the image capture device is controlled immediately, virtually delay-free with respect to at least one recording of the first image data set. This embodiment is based on the fact that it is often desirable e.g. in the case of the electroanatomical mapping system for the trigger signal used during the creation of electroanatomical maps to be linked with the image capture system in order to trigger e.g. x-radiation simultaneously in order to insert graphs from the electronic map into the "live" x-ray images. In this case the Carto system itself, through its operational connection to the patient's ECG, constitutes the abovementioned means of acquiring periodic recurring current information of the periodically moving area and for acquiring information concerning the recording instant of the first image data set. The trigger signal of the electroanatomical mapping system is in this case used immediately and directly to activate the image capture system. In this way, 2D x-ray images are simultaneously generated quasi in real-time, i.e. delay-free, in parallel with the electroanatomical map in order to insert the graph of the electroanatomical map into them.

The object is further achieved by a method for synchronizing an image capture device, wherein said image capture device is used for recording a second image data set of a periodically moving area, said second image data set to be synchronized with at least one older first image data set of the area, each first image data set containing information as to the point in time, relative to the periodically moving area, when recording took place, and characterized in that, with computer assistance, at least one triggering instant $T_{A\_Bd2}$ is derived from periodically recurring, current information of the area and information concerning the recording instant of the first image data set, said triggering instant controlling at least one recording by the image capture device of the second image data set in such a way that the second image data set contains image data synchronized to the first image data set.

In a variant whereby the first, generally pre-operative image data set contains ECG-triggered CT, MR, ultrasound or PET images, the following steps are carried out according to the invention. In a first step the ECG information of the first image data set is read in. If the abovementioned recording methods are involved, the necessary information is obtained from the relevant entries of the DICOM file. In a next step the synchronization zero point $T_{R\_Bd1}$, which will generally be the instant of the R-spike, and the triggering instant $T_{A\_Bd1}$, the point in time at which the recordings of the image data set took place, are determined. The shift time $t_{Ver}$ is calculated therefrom as the difference between synchronization zero point $T_{R\_Bd1}$ and triggering instant $T_{A\_Bd1}$. According to the proposed method, the patient's current ECG is read in and the synchronization zero point $T_{R\_Bd2}$ at the instant of the R-spike is determined. The triggering instant $T_{A\_Bd2}$, which is critical for activating the image capture device, now results from the shifting of the synchronization zero point $T_{R\_Bd2}$ by the previously determined shift time $t_{Ver}$. It shall be understood that, because of the specific image capture device to be activated, it may be necessary to additionally apply to the triggering instant $T_{A\_Bd2}$ thus determined a hold-back time corresponding to the image capture device in order to compensate any delays caused by the image processing system itself. In addition, it may be sufficient not to activate the image capture device at every triggering instant $T_{A\_Bd2}$ for recording a synchronized second image data set, but to use only multiples of this trigger time for image recording.

BRIEF DESCRIPTION OF THE DRAWINGS

The invention will now be explained in greater detail with reference to exemplary embodiments and the accompanying drawings in which:

FIG. 1 shows an example of a device for synchronizing a medical image capture device and FIG. 2 shows the formation of the trigger signal for activating the image capture device using an ECG signal

DETAILED DESCRIPTION OF THE INVENTION

The image capture device 1 shown in FIG. 1 is used for recording a second image data set 2 of a patient P that is synchronized to a first image data set 3. An x-ray tube 10 is operated by an x-ray generator 11. The x-ray tube 10 emits an x-ray beam 12 which passes through a patient P in the area under examination 8 and is incident on an x-ray detector 13 in attenuated form depending on the transparency of the patient P and creates an x-ray image. The absorption of the x-radiation 12 by the patient P follows an exponential function. The x-ray detector 13 converts the x-ray image into electrical signals and produces a second image data set 2. In an associated digital image processing system 14, the second image data set 2 and the first, generally pre-operative image data set 3 are processed and made available to one or more output units 15 to reproduce an overlaid image. In order that the image capture device 1 then only generates recordings that are in synchronism with the first image data set 3, the x-ray generator 11 is activated with time $T_{A\_BD2}$, the triggering time of the second image data set 2. Via the other components involved, this activation causes a second image data set 2 to be generated only at this point in time, triggering at another point in time not being provided, but could be performed manually by the operation team.

The initiation or triggering time $T_{A\_BD2}$ is calculated in a central unit 5a and fed out therefrom via an optional changeover switch 16 to the x-ray generator 11. For this purpose the central unit 5a receives, based on the first image data set 3, information 4 as to the point in time, relative to the periodic movement of the patient P, when recording of the first image data set 3 took place. For many recording methods (CT, MR, ultrasound, PET), the saving and storing of the image data set conforms to the DICOM standard and the information 4 is provided by the DICOM header. As shown in FIG. 1, the central unit 5a can also receive the required information 4 concerning the recording instant of a plurality of different image data sets 3 and if necessary switch between same. As an additional input signal, the central unit 5a receives current ECG information 7 from which said central unit 5a can derive information concerning the state of cardiac motion. For this purpose the patient P is connected to the ECG 6 during the procedure. In the simplest case, the ECG 6 delivers a periodic signal at the instant of the R-spike (synchronization zero point) as ECG information 7 to the central unit 5a. However, other periodic signals at other points in time are also possible. In such a case, however, the central unit 5a must also to be supplied via the ECG information 7 with a shift signal with respect to the synchronization zero point. Although identified and described as a separate unit in this example, the central unit 5a need not necessarily constitute a separate unit. For example, it would be quite conceivable and within the meaning of the invention for the described central unit function to be incorporated in other computer units (e.g. digital image processing system 14). In another variant, FIG. 1 additionally shows an electroanatomical mapping system 5b which because of its operational use is connected to the ECG system 6 and receives via a link the ECG information 7 which controls the electroanatomical mapping system. The mapping system generates its first image data set 3 and controls in parallel thereto the x-ray generator 11 of the image capture device 1 using the information 4 as to the point in time, relative to the periodic movement of the patient P, when recording of the image data set 3 takes or took place, as an initiation or triggering time $T_{A\_BD2}$. This trigger signal is forwarded to the image capture system 1 via the optional changeover switch 16. For overlaying with the second image data set 2 produced by the image capture device 1, the image data set 3 generated by means of the electroanatomical mapping system 5b is forwarded to the digital image processing system 14 for display on the output unit 15. According to the invention, the device can either have only the means 5a or only the means 5b of acquiring periodically recurring current information 9 of the area 8 as well as the information 4 concerning the recording instant of the first image data set 3, parallel operation of the two also being possible, however. In the case of parallel operation the changeover switch 16 is implemented for automatic or manual switching.

FIG. 2 shows the steps of the method according to the invention using the example of a first image data set 3 which has been produced in accordance with the DICOM standard. The information 4 as to the point in time, relative to the periodic movement of the patient P, when the first image data set 3 was produced consists in this case of an extract of the DICOM header 7. The shift information $t_{Ver}$ is derived therefrom. The time $t_{Ver}$ results from the difference between the synchronization zero point $T_{R\_Bd1}$ at the instant of the R-spike of the first image data set 3 and the triggering instant $T_{A\_Bd1}$ (generally in a resting phase of the heart) of the first image data set 3. In another step the current ECG 6 of the patient P is read in. In this example, the current ECG 6 of the patient P feeds out a synchronization signal at the instant of the R-spike of the patient ECG 6 (synchronization zero point). The activation instant for the generation of the second image data set $T_{A\_Bd2}$ results from the shifting of the synchronization zero point $T_{R\_Bd2}$ by the shift time $t_{ver}$.

The invention claimed is:

1. A device for synchronizing a second image data set of a periodically moving area of a patient with a first image data set of the periodically moving area, wherein the periodically moving area moves in distinct phases over each period, comprising:
   a computing unit for
      (a) receiving a first image data set comprising previously recorded 3D image data recorded in a particular phase of movement, wherein the 3D image data further comprises phase information stored therewith as to when recording of the 3D image data took place relative to the period of periodically moving area,
      (b) extracting the phase information and deriving a shift time calculated from a difference between a triggering instant when recording of the 3D image data took place and a synchronization zero point relative to the period of periodically moving area, and
      (c) receiving current phase information regarding a current period of the periodically moving area and deriving a current synchronization zero point relative to the current period of periodically moving area, the computing unit automatically deriving a current triggering instant from the shift time derived from the first data set and the current synchronization zero point;
   an image capture device that records a second image data set, wherein the current capturing is triggered by the current triggering instant automatically derived from the first data set, so that the second image data set is synchronized with the first image data set upon capture; and
   a digital image processing system for producing an overlaid image comprising the second image data set combined with the first image data set.

2. The device as claimed in claim 1, wherein the triggering instant is a single triggering instant within a periodic period of the periodically moving area.

3. The device as claimed in claim 1, wherein the first image data set is recorded at a plurality of different recording instants within a periodic period of the periodically moving area and a plurality of respective current triggering instants relative to the current period of periodically moving area are derived accordingly.

4. The device as claimed in claim 1, wherein the first image data set is a pre-operative image data set of the periodically moving area of the patient.

5. The device as claimed in claim 1, wherein the first image data sets is recorded by a plurality of different image recording methods.

6. The device as claimed in claim 5, wherein the acquiring device switches the first image data sets between the different image recording methods.

7. The device as claimed in claim 1, wherein the acquiring device is an electroanatomical mapping system.

8. The device as claimed in claim 7, wherein the first image data set is generated by the electroanatomical mapping system.

9. The device as claimed in claim 8, wherein at least one recording of the second image data set is recorded immediately with respect to at least one recording of the first image data set.

10. The device as claimed in claim 1, wherein the recording instant of the first data set is relative to a periodic period of the periodically moving area.

11. A method for synchronizing a second image data set of a periodically moving area of a patient with a first image data set of the periodically moving area of the patient, comprising:

receiving a first image data set comprising previously recorded 3D image data recorded in a particular phase of movement, wherein the 3D image data further comprises phase information stored therewith as to when recording of the 3D image data took place relative to the period of periodically moving area, extracting the phase information and deriving a shift time calculated from the difference between a triggering instant when recording of the 3D image data took place and a synchronization zero point relative to the period of periodically moving area;

acquiring a current phase information regarding a current period of the periodically moving area and deriving a current synchronization zero point relative to the current period of periodically moving area;

automatically calculating a current triggering instant from the shift time derived from the first data set and the current synchronization zero point;

triggering an image capture device to record the second image data set at the current triggering instant automatically derived from the first data set, so that the second image data set is synchronized with the first image data set upon capture; and producing an overlaid image comprising the second image data set combined with the first image data set.

12. The method as claimed in claim 11, wherein the triggering instant derived from the first data set is relative to a periodic period of the periodically moving area.

13. The method as claimed in claim 11, wherein the first image data set is a pre-operative image data set of the periodically moving area of the patient.

14. The method as claimed in claim 11, wherein the first image data set comprises an image selected from the group consisting of: CT, MR, ultrasound, and PET.

15. The method as claimed in claim 11, wherein the first image data set comprises information of the recording instant relative to a periodic period of the periodically moving area.

16. The method as claimed in claim 15, wherein the information of the recording instant is an ECG information of the first image data set.

17. The method as claimed in claim 16, wherein the current information of the periodically moving area is a current ECG information of the patient.

18. The method as claimed in claim 17, further comprising:
reading-in the ECG information of the first image data set,
determining the synchronization zero point, the triggering instant, and the shift time from the ECG information of the first image data set,
reading-in the current ECG information of the patient,
determining the current synchronization zero point from the current ECG information of the patient, and
calculating the current triggering instant by shifting the second current synchronization zero point with the shift time.

19. The method as claimed in claim 18, wherein the synchronization zero point is an instant that a R-spike occurs in the ECG information of the first image data set.

20. The method as claimed in claim 18, wherein the current synchronization zero point is an instant that a R-spike occurs in the current ECG information of the patient.

* * * * *